United States Patent [19]

Pilgeram

[11] 4,245,040
[45] Jan. 13, 1981

[54] DETECTION AND MEASUREMENT OF CIRCULATING FIBRIN

[76] Inventor: Laurence Pilgeram, P.O. Box 1583, Goleta Station, Santa Barbara, Calif. 93017

[21] Appl. No.: 962,302

[22] Filed: Nov. 20, 1978

[51] Int. Cl.³ .......................... C12Q 1/56; C12Q 1/48; C12Q 1/38
[52] U.S. Cl. ......................................... 435/13; 435/15; 435/23
[58] Field of Search ...................... 435/13, 15, 18, 23; 195/103.5 R

[56] References Cited

U.S. PATENT DOCUMENTS 3,294,641  12/1966  Lorand .............................. 435/13 X

OTHER PUBLICATIONS

Kisker et al., *J. Clin. Invest.*, 50, (1971), 2235–2241.

Buluk et al., Chemical Abstracts 68: 47578p, (1968), p. 4593.

*Primary Examiner*—Esther M. Kepplinger

[57] ABSTRACT

An improved method is described for the detection and quantitation of Circulating Plasma Fibrin, also known as Soluble Fibrin (Fs), which is based upon the specific enzymatic transfer by Factor XIII, or Papain, of a Carbon-14 label in Glycine Ethyl Ester to Fs and which is improved upon by (a) substitution of the enzyme reaction in whole plasma for the enzyme reaction in an alcohol fraction of plasma, (b) inclusion of a serum blank to correct for low level non-specific labeling of plasma protein other than Fs, and (c) substitution of molecular, or gel, filtration for purification of Fs by chemical fractionation. The preceding improvements reduce the operational time for the assay from 72 hours to 4 hours, and reduce the labor time for the assay from 12 hours to 1 hour.

3 Claims, No Drawings

DETECTION AND MEASUREMENT OF CIRCULATING FIBRIN

MEASUREMENT OF CIRCULATING FIBRIN

This invention relates to rapid and specific measurement of circulating fibrin (Fs), also known as soluble fibrin, based upon the combination of specific enzymatic radio-isotope labeling of Fs and molecular filtration.

It is known to use the enzyme called fibrin stabilizing factor (Factor XIII) with glycine-C14 ethyl ester to attach an isotopic label to Fs (Lorand, L., in Fibrinogen and Fibrin Turnover of Clotting Factors, Editor: F. Koller, F. K. Schattauer Verlag-Stuttgart, 1963; Kisker, C. D. and Rush, R. in Detection of Intravascular Clotting, Journal of Clinical Investigation 50:2235, 1971). The principle has been developed into a sensitive and specific method for measuring the plasma level of Fs or intravascular fibrin formation and detecting patients with or at risk of thrombosis with a diagnostic accuracy better then 93 percent (Pilgeram, L., Karl Thomae Award Address, Thrombosis Diathesis Haemorrhagica 31:245,1974; Pilgeram, L. and von dem Bussche, G., Radio-Assay of Circulating Soluble Fibrin, Symposium: Radio Isotope Techniques in Blood Coagulation and Fibrinolysis, Proceedings of the IV Congress of the International Society on Thrombosis and Haemostasis, Wien, Austria, 1973).

The foregoing method, cited above, is time consuming requiring about 72 hours from inception to completion. The method is complex and tedious being based upon chemical purification techniques and it is therefore difficult to achieve adequate reproducibility in the hands of non-research personnel.

It is the object of the present invention to provide a method by which the time from inception to completion of the assay may be reduced from 72 hours to less than four (4) hours, to reduce the labor from more than 12 hours to less than one (1) hour, and to retain and improve on the specificity and sensitivity based upon enzymatic labeling of Fs.

In accordance with the invention, this object is achieved by:

(a) Combining Factor XIII, or Papain, induced glycine-C14 ethyl ester labeling of Fs with membrane filtration and purification of C14 labeled Fs, and (b) Substituting the enzyme reaction in whole plasma for enzyme reaction with the 8 percent cold ethanol plasma fraction, and correcting for non-specific labeling with an enzyme reaction in a serum blank, or (c) Combining Factor XIII, or Papain, induced glycine-C14 ethyl ester labeling of Fs with gel filtration and purification of the C14 labeled Fs.

Unlike the published method, this process does not depend upon clotting and repetitive manual chemical dissolving and precipitation of fibrin for the purpose of purifying fibrin prior to determination of the magnitude of radio isotope label.

Unlike the published method, the isotopic labeling procedure excludes the 8 percent ethanol precipitation step of fibrin, which is not quantitative, and substitutes a reaction in whole plasma and a serum blank which corrects for any non-specific isotopic labeling of proteins other than Fs.

By membrane filtration is meant the filtration of the plasma-enzyme-isotope incubated mixture through synthetic membranes which pass micro-solutes and water freely and cut-off molecules with a molecular weight greater than 10,000.

By gel filtration is meant the filtration of the plasma-enzyme-isotope incubated mixture through spherical agarose gels which separate Fs-C14 from glycine-C14 ethyl ester and other contaminants.

The invention is illustrated by the following examples: Nine parts of blood are added to a polystyrene centrifuge tube containing one part of an anticoagulant mixture consisting of heparin (10 u) and 10 mg/ml soybean trypsin inhibitor (SBTI) dissolved in 0.06 M TRIS, 0.3 M NaCl buffer, pH 7.6. The sample is centrifuged at 6000 rpm in a refrigerated centrifuge for 10 min at 0 C. To 0.8 ml of the supernatant platelet-poor plasma are added 0.1 ml glycine-C14 ethyl ester (5–20 uc) (specific activity: 9.0 mc/mM) and 0.1 ml activated Factor XIII (3 units), or Papain, dissolved in 0.06 M TRIS, 0.3 M NaCl buffer, pH 7.6. The mixture is incubated for 30 min at 37 C after which 0.1 ml of 0.25 M EDTA is added to stop the action of the enzyme. The serum blank is processed according to the procedure outlined for plasma. Serum is prepared from the native blood sample by allowing blood to clot in the presence of one part SBTI (10 mg/ml) to nine parts of blood. The mixtures are then individually subjected to molecular filtration or gel filtration.

Example 1: This Example illustrates the application of molecular filtration. Molecular filtration may be performed with a number of commercially available filters or filter assemblies. The plasma-enzyme-isotope mixture is diluted to 5 ml with TRIS buffer (0.06 M TRIS, 0.3 M NaCl, pH 7.6) and added to a membrane cone manufactured by Amicon. * This cone is subjected to centrifugation (RCF<1000 G) at 4 C for 10 minutes. The sediment is resuspended in 5 ml TRIS-NaCl buffer and recentrifuged. Six repetitions of centrifugation and resuspenion are sufficient to reduce the retentate level of glycine-C14 ethyl ester radio activity to background counting rates. The retentate containing Fs-C14 is then subjected to liquid scintillation counting of the radioactivity and the total count determined. The total count is converted to nano or micro moles of Fs based upon standard curves.

*Amicon, Lexington, Massachusetts. Other membranes may be substituted, e.g., immersible filter by Millipore, Bedford, Massachusetts.

Example 2: This example illustrates the application of gel filtration. Gel filtration is achieved by passing the plasma-enzyme-isotope incubated mixture through a glass column of spherical agarose gel with an exclusion limit of $150 \times 10^6$ Daltons**. Elution is processed with 0.06 M TRIS, 0.3 M NaCl buffer, pH 7.6. Samples are collected in a fraction collector. The eluate, containing Fs-C14, is counted by liquid scintillation counting and the count converted to nano or micro moles of Fs based upon standard curves. In some cases the molecular weight and configuration of the fibrin polymer exceeds the pore size of the specified gel and is trapped. In these cases, the trapped fibrin is released by 2 percent monochloroacetic acid or 5 M urea and then counted.

**This preparation is commercially available, e.g., BioRad, Richmond, CA.

The results of the application of the Fs assay process to human plasma are presented in Table I.

TABLE I

| | Molecular Filtration | Gel Filtration |
|---|---|---|
| | Nano Moles Fs/ml Plasma* | |
| Plasma (Normal)** | 220 ± 48 | 185 ± 47 |
| Plasma + Fibrinogen (3.5 mg/ml) | 214 ± 44 | 182 ± 42 |
| Plasma (No Factor XIII or Papain) | 0 | 0 |
| Serum | 19 ± 10 | 18 ± 8 |
| Serum + Thrombin ($10^{-5}$ u/ml) | 20 ± 11 | 19 ± 7 |
| Plasma + Thrombin ($10^{-5}$ u/ml) | 810 ± 89 | 756 ± 78 |
| Plasma + Thrombin ($10^{-2}$ u/ml) | 1080 ± 95 | 980 ± 89 |
| Plasma (Coronary Thrombosis)*** | 1669 ± 140 | 1245 ± 128 |
| Plasma (Thrombotic Stroke)**** | 1548 ± 133 | 1131 ± 121 |

*Calculation based upon the assumption of a ratio of one to one in the labeling of Fs with glycine-C14 ethyl ester. All values corrected for serum blank. Twenty uc of glycine-C14 ethyl ester were used in these studies.
**Fasting plasma obtained from 48 normal males, age range: 22-57 yrs.
***Fasting plasma obtained from 28 males (5 months post coronary infarct, no anti coagulation.
****Fasting plasma obtained from 26 males (6 months post thrombotic stroke, therapy = aspirin or dipyridamole.

These Examples illustrate specificity of the assay process for circulating fibrin by the minimal labeling of serum in the absence of fibrin, by the absence of labeling of fibrinogen, by the increase in uptake of label in the presence of thrombin and plasma or fibrin, by the absence of significant uptake of label in the presence of thrombin and serum, and by the increase in uptake of label in patients known to suffer from hypercoagulable states.

These Examples illustrate improved specificity where correction is made for non-specific labeling of non Fs proteins by subtracting the low degree of labeling in serum.

These Examples illustrate improvement in time and labor saving where Start-Finish, or operational, time is reduced from 72 hours to less than 4 hours and labor time is reduced from 12 hours to less than 1 hour.

These Examples illustrate improved sensitivity and quantitation where enzyme labeling of the plasma 8 percent cold ethanol precipitate was replaced with labeling of whole plasma thereby increasing the uptake of label into Fs moieties by 8-22 percent, average = 11 percent.

These Examples illustrate improved recovery of labeled Fs where isolation of Fs by multiple chemical steps of clotting, solubilization, and reprecipitation are replaced by physical molecular filtration based upon molecular size. Comparison of recovery between the two processes showed the chemical process to lose up to 18 percent of the label which was present when assayed by molecular filtration.

I claim:

1. In the process for the detection and quantitation of circulating plasma fibrin (Fs) comprising incubation at 37° C. of glycine-C14 ethyl ester and Factor XIII, or papain, with an 8 percent ethanol fraction of plasma, recovery of C14 labeled fibrin and measurement thereof, the improvement comprising substitution of whole plasma for the 8 percent ethanol fraction.

2. The improvement in the assay as claimed in claim 1, wherein the recovery and purification of C14 labeled fibrin is performed by physical molecular or gel filtration.

3. An improvement in the assay as claimed in claim 1, wherein the measurement step includes use of a serum blank to correct for labeling of plasma proteins other than fibrin.

* * * * *